United States Patent [19]

Weissman

[11] Patent Number: 4,954,082
[45] Date of Patent: Sep. 4, 1990

[54] RECIPROCATING DENTAL TOOL

[76] Inventor: Bernard Weissman, 225 E. 48th St., New York, N.Y. 10017

[21] Appl. No.: 179,332

[22] Filed: Apr. 8, 1988

[51] Int. Cl.⁵ .............................................. A61C 17/02
[52] U.S. Cl. ........................................ 433/80; 433/87; 433/90; 433/118; 433/125; 433/128
[58] Field of Search ..................... 433/80, 82, 87, 90, 433/118, 119, 120, 121, 122, 123, 124, 125, 128, 165, 166; 222/92

[56] References Cited

U.S. PATENT DOCUMENTS

| | | | |
|---|---|---|---|
| 1,797,686 | 3/1931 | Homer | 222/92 |
| 2,300,828 | 11/1942 | Goldenberg | 433/166 |
| 3,930,173 | 12/1975 | Banko | 433/119 |
| 4,173,828 | 11/1979 | Lustig et al. | 433/122 |
| 4,266,933 | 5/1981 | Warden et al. | 433/82 |
| 4,781,589 | 11/1988 | Bareth | 433/122 |

Primary Examiner—John J. Wilson
Attorney, Agent, or Firm—Paul J. Sutton; Barry G. Magidoff; Anthony Amaral, Jr.

[57] ABSTRACT

There is provided a dental tool for use with a reciprocating drive means and a sleeve member operatively connected to the drive means for reciprocating motion and designed to retain a dental tool, the dental tool comprising a shank portion designed to be retained for reciprocating movement by the sleeve member of the handpiece, and a dental blade, preferably with an abrasive surface, secured to one end of the shank; in one embodiment, the dental tool is preferably hollow and further comprises an axially extending channel, preferably extending along the full length of the shank and a plenum extending within the dental blade, and outlet perforations from the plenum extending through the blade, and in a second embodiment there is further provided means secured to the shank portion for spplying pressure within the channel to force any fluid material within the channel and plenum out through the outlet perforations through the blade. Finally, there is provided means for dispensing fluid material, e.g., a cleaning paste, into the shank channel comprising syringe means having a reservoir section and pressure applying means for injecting fluid within the reservoir into the shank of the tool. Preferably, the tool further comprises rotation restraining means, such as an elastically deformable stop member, for providing limited resistance to rotation of the dental tool while it is being subjected to reciprocating motion and the application of axial force during dental therapy.

17 Claims, 11 Drawing Sheets

RECIPROCATING DENTAL TOOL

BACKGROUND OF THE INVENTION

The present invention relates to a motor-driven, reciprocating dental tool which provides means to safely prevent undesirable rotation of the tool during use and further provides sanitary means for simultaneously applying a fluid medium, such as dental cleaning paste, to teeth while mechanically treating, such as cleaning or polishing the teeth by abrasion, and more particularly while mechanically providing reciprocating motion to an abrasive member through which the fluid paste is simultaneously applied.

There has previously been successfully provided a mechanically driven hand tool, which can be readily powered by a conventional rotary dental drill, to provide reciprocating motion of the type preferably used when abrading or filing teeth or removing excess restorative material, such as hardened dental amalgamsor dental composite materials. Such abrasive methods, depending upon the hardness of the abrasive material and the rapidity and pressure with which the abrading surface is applied, can be used to either remove hardened amalgam or dental enamel or to merely remove plaque and to clean and polish teeth surfaces, including both the major lingual and facial surfaces of teeth as well as the proximate faces bordering the teeth interspaces.

The reciprocating handpiece, such as the device described in U.S. Pat. No. 3,552,022 to Axelsson, and commercially available as a Dentatus EVA Reciprocating Motor Driven Handpiece, has been used for both purposes, together with the dental abrasive tools formed of, e.g., hardened or diamond coated metal blades or plastic blades with or without embedded abrasives.

It is also known to utilize a syringe type of device to apply toothpaste and the like material for dental hygienic cleaning prior to application of either a mechanically driven or manually operated tooth cleaning means, whether for clinical use or for home use. Such a device is shown, for example, in U.S. Pat. No. 4,411,623 to Axelsson.

SUMMARY OF THE INVENTION

It is an object of the present invention to provide a means for simultaneously applying a cleaning or abrading fluid or other therapeutic medium to teeth while mechanically abrading or polishing the teeth using a mechanically driven tool. It is a further object of the present invention to continuously administer such fluid medium through a disposable mechanically driven abrading tool which can be hygienically filled and refilled during a single continuing procedure. The tool can be molded sufficiently economically for a one-time use, thus further reducing any risk of contagious infection.

It is also an object of the present invention to restrain rotation of the blade under normal therapeutic force, so as to permit accurate positioning and manipulation of the tool, while preventing injury from the accidental application of excessive force.

The fluid dispensing and reciprocating abrading tool of the present invention for simultaneously applying, e.g., a cleaning fluid, paste, medicament, such as a fluoride solution, or a cooling fluid, and providing the reciprocating abrading action, comprises a mechanically driven dental handpiece for providing reciprocating drive means, and a removable, hollow, dental abrading tool, the dental tool comprising a shank, operatively, directly, but removably connected to the dental handpiece and having a central channel extending axially therealong, and a blade member secured to the shank and comprising an interior plenum chamber in fluid flow connection with the shank channel and a multitude of with fluid outlet perforations through the blade surface. Fluid pressure means are provided for causing the flow of cleaning fluid from the shank channel through the blade plenum and out the perforations. When the outer opening of the shank channel is closed off, pressing the flexible walled hollow blade between two teeth will cause discharging of fluid, such as a cleaning paste.

Limited restraining means are provided in another preferred embodiment of this invention for restraining rotation of the blade during operation, while providing for movement upon the application of a greater then maximum permitted force; at such greater force, the restraint breaks away and the tool blade is permitted to rotate to avoid injury to the patent. Such rotation restraint is provided by interaction between the tool blade and the reciprocating dental handpiece.

BRIEF DESCRIPTION OF THE DRAWINGS

Preferred embodiments of this invention are further described below, by way of example and not exclusion, by reference to the accompanying drawings which display certain portions of the present invention in schematic form. The details of such schematically shown portions will be readily known to those skilled in the art based upon the following verbal descriptions. Referring to the drawings.

DETAILED DESCRIPTION OF PREFERRED EMBODIMENTS:

The dental tool of the present invention is to be used and applied in combination with a conventional commercially available drive head which is improved in accordance with the present invention. Such a drive head comprises conventional driving elements which do not, in themselves, form a part of the present invention and, thus need not be illustrated in great detail. Examples of suitable driving means are shown, for example, in U.S. Pat. Nos. 3,552,022 to Axelsson and 4,629,426 to Levy. Such a device is generally of a sufficiently slender and elongated nature, often having a contra-angle head, to enable a dentist to easily and without injury to the patient, manipulate the device within the mouth and, most particularly, against even the rear molars. However, as such a device is conventional, it will not be described herein in greater detail than is shown in the drawings and can be determined from the prior disclosures.

Referring to FIGS. 1–5 and 14–15, as a group, the dental tool itself, generally indicated by the numeral 4, is elongated, pointed and flat in cross-section, such that a longitudinal but slanted edge 28 is formed between the two major surfaces 27 of the blade 7. The tool, including both the shank 10 and stiffening spine 8 and the blade 7, is hollow to provide a reservoir and channel for the passage of fluid material. As shown, the stiffening spine 8 of the blade 7 does not extend to the end of the blade; the flat blade portion 7 extends both longitudinally and laterally outwardly from the spine 8. The blade 7 has substantially parallel sides 27, although the sides 27 can be slightly convergent towards the edge 28, if desired. Along the blade edge 28 and the blade side surfaces 27, are provided perforations 18 extending fully through the blade material and into the interior hollow space, defined by the interior surfaces 17 within the blade 7. This interior space 17 is directly open to the hollow channel defined by shank channel surfaces 16 extending to the top of the shank 10. Preferably, the minimum width at the blade edge 28 should not be less than about 0.01 in., if outlets 18 are provided at the edge 28, in order to provide sufficient interior space for passage of a fluid.

Figure 14:
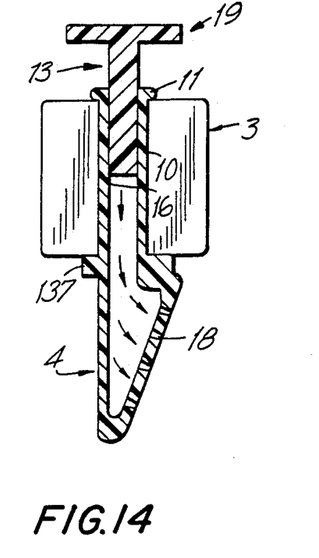
FIG. 14 is a cross-sectional schematic diagram of a fluid dispensing tool of the present invention inserted in a reciprocating sleeve.
Figure 15:
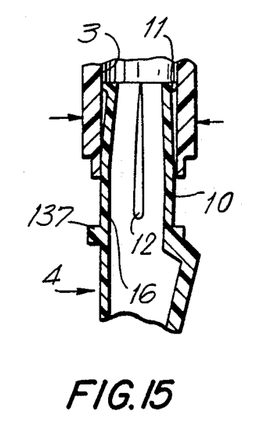
FIGS. 15 and 16 are partial schematic cross-section views depicting the insertion and securing of a dental tool into a reciprocating sleeve in accordance with the present invention.
Figure 16:
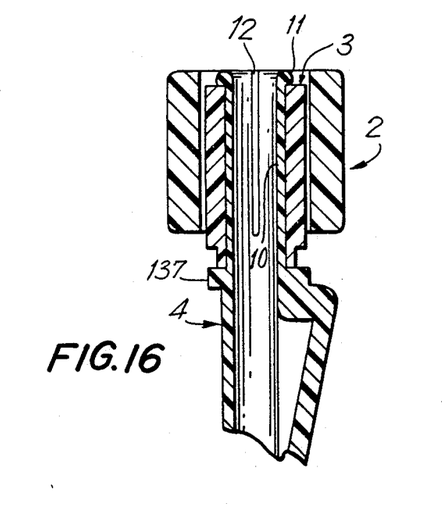

The material forming the shank 10 is molded such that it is sharply thinner at least at two locations to define grooves 12. These grooves 12 permit easy folding together of the shank 10 when it is being inserted into the sleeve 3; the grooves 12 are covered by a thin membrane, preferably coextensive with the outer surface of the shank 10, to maintain the integrity of the fluid flow by preventing leakage of fluid from the central channel 16. Around the top of the shank 10 is a retaining lip 11. The dental tool 4 is slip fitted into a sleeve 3 reciprocatingly held within a head 2 of a dental handpiece 1, for example, as shown in FIGS. 14 and 15, which provides for reciprocating movement. The tool holding sleeve 3 is in the form of a hollow cylinder defining a bore into which the tool shank 10 is fitted.

Figure 2:
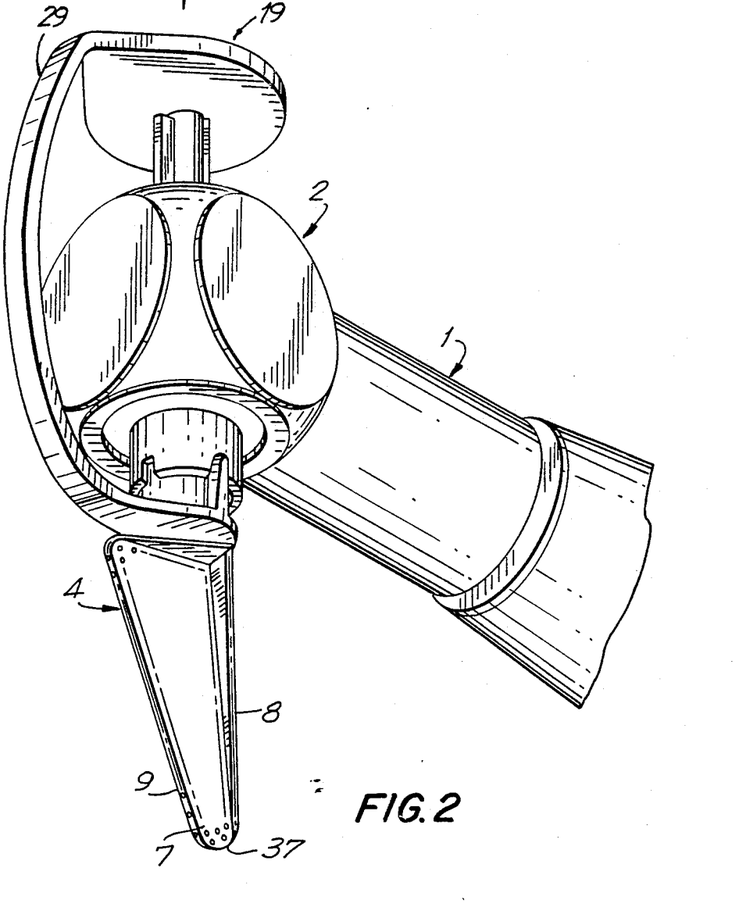
FIG. 2 is an isometric view showing a fluid dispensing file blade in accordance with the present invention and the head of a reciprocating dental handpiece.
Figures 2A, 3:
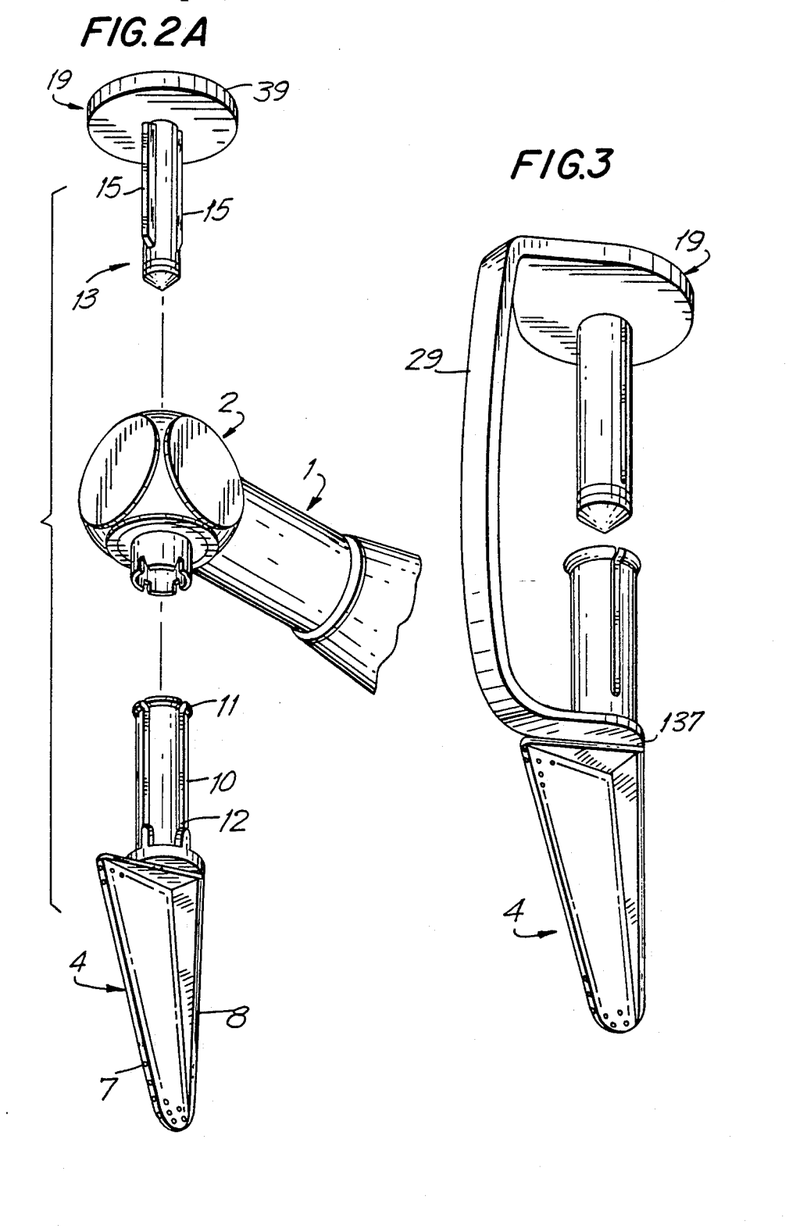
FIG. 2a is an exploded view of the device of FIG. 2.
FIG. 3 is an isometric view of another embodiment of a fluid dispensing file blade in accordance with the present invention.

In the embodiment shown in FIG. 2, the tool holding sleeve 3 is provided with one or more notches at its end proximal the tool blade 7, defined by concave surfaces 6. When the tool 4 is installed in the sleeve 3, a resilient spur 5 formed on one side of the shank 10 adjacent the blade 7 is juxtaposed within the notch 6 (as shown in detail in FIG. 19) to prevent rotation of the tool 4 during use.

The manner of driving the reciprocating sleeve 3 is shown for example, in U.S. Pat. Nos. 3,552,022 or 4,629,426. It is also known to prevent rotation of the tool holding sleeve 3, as described in U.S. Pat. No. 4,582,060 during reciprocating motion.

The tool is preferably formed of a polymer or elastomer and the thickness of the walls 27 of the blade 7 is preferably not greater than about 0.015 in. and most preferably in the range of from about 0.005 to about 0.01 in. This thickness, together with the reinforcing spine 8, is sufficient to prevent excessive flexibility or folding during use of the major part of the blade, whereas the outer point 37 is of greater flexibility as it extends beyond the end of the spine 8. Such thin, flexible blade is well adapted to being inserted into the dental interspaces for e.g., polishing, cleaning, abrading and shaping, or applying medication.

A pressure feed cap generally indicated by the numeral 19 is formed integral with the tool via a strap 29 extending from the flange 129 intermediate the blade 7 and the shank 10. The cap 19 comprises a plunger 13, and an outer button 39 secured thereto and having a flat outer surface. The plunger 13 also includes splines 15 which extend longitudinally along and radially outwardly from the plunger 13 and are juxtaposed so as to engage the grooves 12 through the shank 10, when the plunger 13 is slip-fitted within the central shank channel 16; the plunger 13 creates a piston action as it is pressed into the channel 16 by finger pressure on the cap outer surface 39. The outer cap surface 39 preferably is shaped and textured for improved fingertip control.

Figure 20:
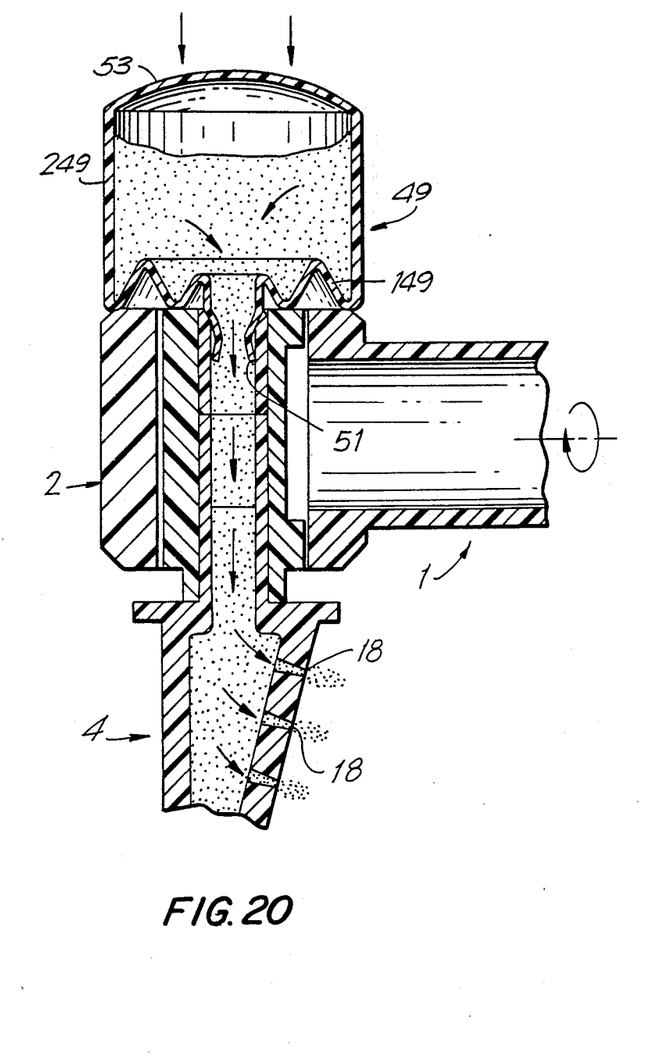
FIG. 20 is a cross-section view of a dispensing reservoir for a dental tool of the present invention.

An alternative form of fluid pressure means is provided by the flexible reservoir, generally indicated by the numeral 49, in FIG. 20. Reservoir 49 has a spout 51 which is inserted into the end of a tool shank 10. The spout 51 can be secured to the shank 10 by a threaded joint or by a tight slip fit. The reservoir 49 includes a corrugated wall 149, forming a bellows, on the lateral wall adjacent the handpiece head 2, (as shown in FIG. 20) or as the circumferential wall 249, to permit reciprocating movement of the sleeve 3 and the tool 4, while maintaining the cartridge 49 in a stationary position against the top of the head 2. By maintaining finger pressure along the thin wall membrane 53 at the distal end of the cartridge 49, the reciprocating movement itself will provide a pumping action to force any fluid material, such as tooth paste from within the cartridge 49 into the shank 10 and out the blade perforations 18.

Figure 19:
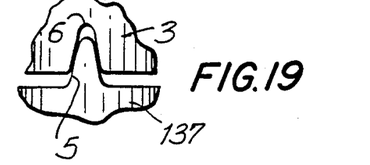
FIG. 19 is an enlarged partial side elevation view enlarged to show the tapered notch and spur rotation-restraining means.

The anti-rotation spur 5 on the tool is preferably tapered, as shown in the enlarged partial cross-section view of FIG. 19, to a narrower thickness at the outer edge. The notch 6 is tapered in a matching fashion to receive the spur 5. This taper, preferably having an angle of from about 10° to about 30°, together with a judicious selection of desired material of construction, permits selecting the desired breakaway turning moment, beyond which the tapered spur 5 will break out of the tapered notch 6 and permit rotation of the tool blade 7, as a safety means to prevent injury to a patient's teeth or mouth.

The tool can be made of polymers or elastomers, such as polypropylene, silicone rubber, or polyurethane. In these preferred embodiments the entire hollow tool 4, including the shank 10 and the blade spine 8 and the blade 7, together with the interior spaces, and perforations, are formed integrally from a single material, as by molding procedures well known to the art.

The major surfaces 27 and leading edge 28 of the tool blade 7 can be formed so as to provide a desired effect. For example, the major surfaces 27 can be formed with a rough grainy surface, or with embedded particles of a harder material than the polymer or elastomer, or even molded with tiny fibers, or tendrils, on the surface, e.g., in the manner in which a so-called Velcro surface is formed.

Figures 4, 4A, 5, 6:
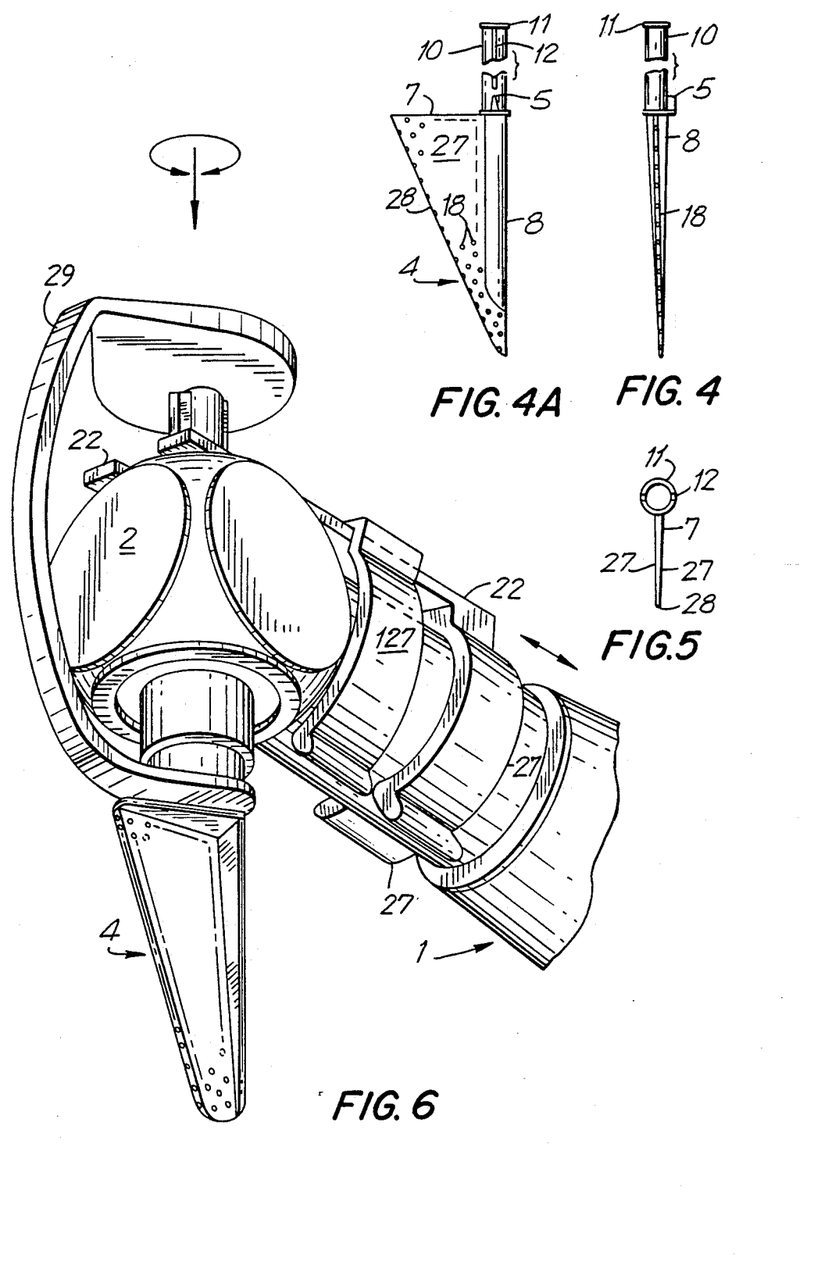
FIG. 4 is a front elevation view of the tool of FIG. 3.
FIG. 4a is a side view of the tool of FIG. 3.
FIG. 5 is a top view of the tool of FIG. 3.
FIG. 6 is an isometric view of an alternative type of fluid-dispensing file blade installed in the head of a reciprocating dental handpiece with an alternative form of a rotation-restraining means.
Figures 7, 8:
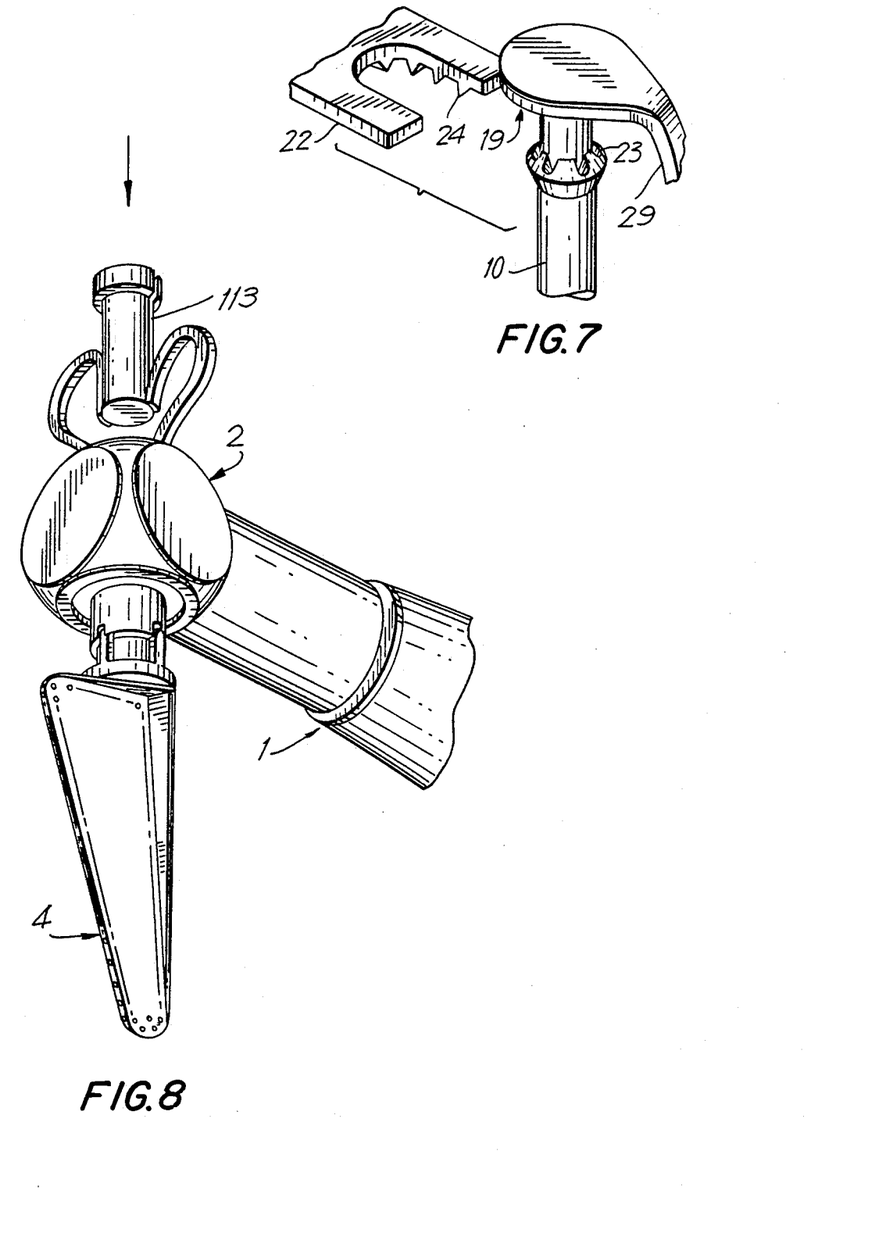
FIG. 7 is a partial isometric view showing the rotation-restraining means in a retracted position.
FIG. 8 is a partial isometric view of a further alternative embodiment of the fluid-dispensing dental tool of the present invention.

In another alternative embodiment, as shown in FIGS. 6 and 7, the rotation-restraint can be manually disengaged. A spring leaf 22 can, for example, be slidably secured to the dental handpiece 1 by a pair of resilient arms 21. At the distal end of the spring leaf 22 from the arms 21 is a cleft 122, and at the apex of the cleft 122 are tapered teeth 24 extending outwardly from the surface of the spring leaf 22 towards the handpiece 1. The end of the collar 11 is provided with matching tapered notches 123 also tapered inwardly. In the engaged position, the leaf spring slides until the tapered teeth 24 are juxtaposed with the shank collar 23 to mate with the notches formed by the concave surfaces 123. When rotational restraint is not desired, the spring leaf 22 can be slidably moved laterally away from the head 2, to disengage the teeth 24 and notches 123. The resilience of the spring leaf 22 and of the collar material 23 can be selected to provide for release of the restraint when a movement greater than the restraint maximum is exerted.

In addition, if desired, the spring teeth 24 and mating notches 123 can be angled in a clockwise or counterclockwise direction, respectively, permitting rotating movement in one direction but restraining movement in the opposite direction of rotation, thus providing a pawl and ratchet effect.

Figure 9A:
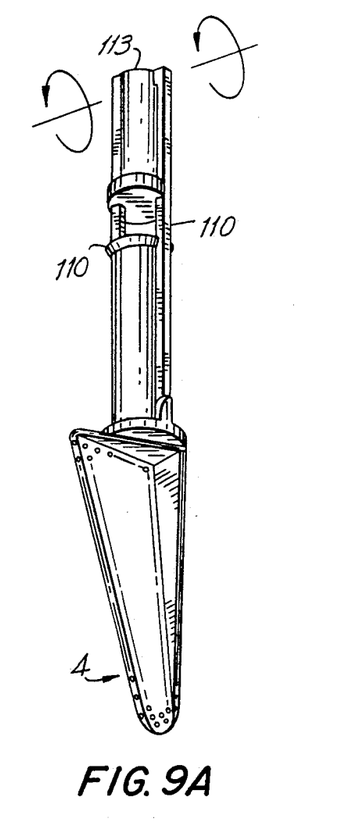
FIGS. 9a and 9b are isometric views of yet another alternative embodiment of a fluid dispensing dental
Figure 9B:
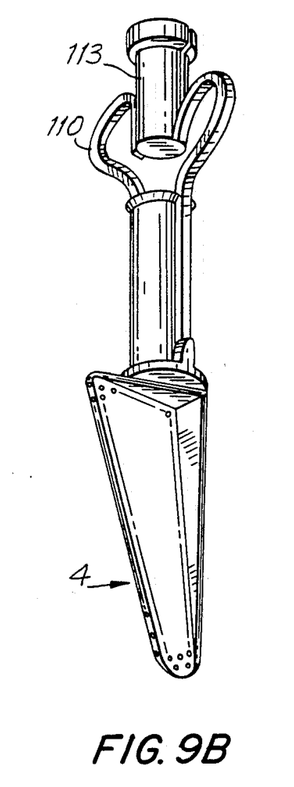

FIGS. 8 and 9 depict an alternative molded tool wherein the plunger is secured via a double strap to the tool shank. In this embodiment, the double straps fold up along the side of the plunger 113, and mate with the grooves formed in the shank 110 of the tool, when the plunger 113 is inserted into the shank channel.

The size of the perforations through the tool blade surfaces are determined based upon the fluid intended to be dispensed. Thus, a thin, non-viscous fluid being passed through the blade preferably should be used with a tool wherein the perforations are not larger than 0.05 mm. in diameter, and most preferably in the range of from 0.03 mm. to 0.05 mm. in diameter. Alternatively, a highly viscous material, such as toothpaste, including the type which contains dispersed abrasive particles, should have larger perforation openings, limited primarily by the particle size of the abrasive particles dispersed within the, e.g., toothpaste. In general, commercially available such materials, e.g., toothpaste, have abrasive particles of a size not larger than about 10 to about 40μ, and thus the perforations should have diameters sufficient to pass such pastes or gels containing such particles without clogging. Preferably, at least five outlet perforations are provided along the slanted blade edge 28, and preferably additional ones are provided over the principal blade surface 27, especially adjacent and at the tip 37.

Figure 21:
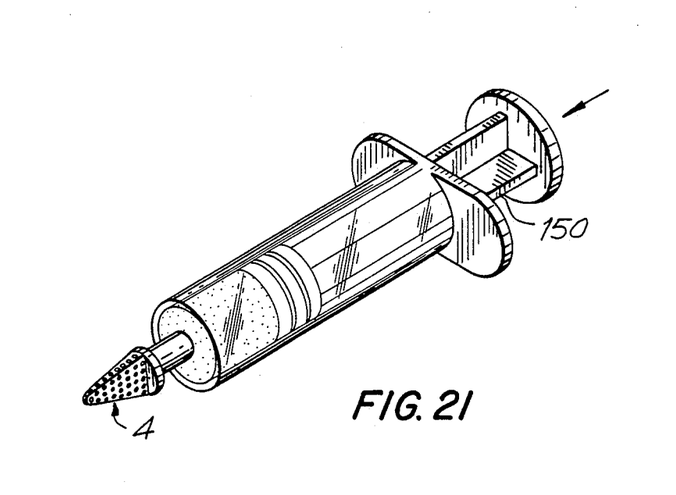
FIG. 21 is an isometric view of a syringe filling a dental tool in accordance with the present invention.
Figure 22:
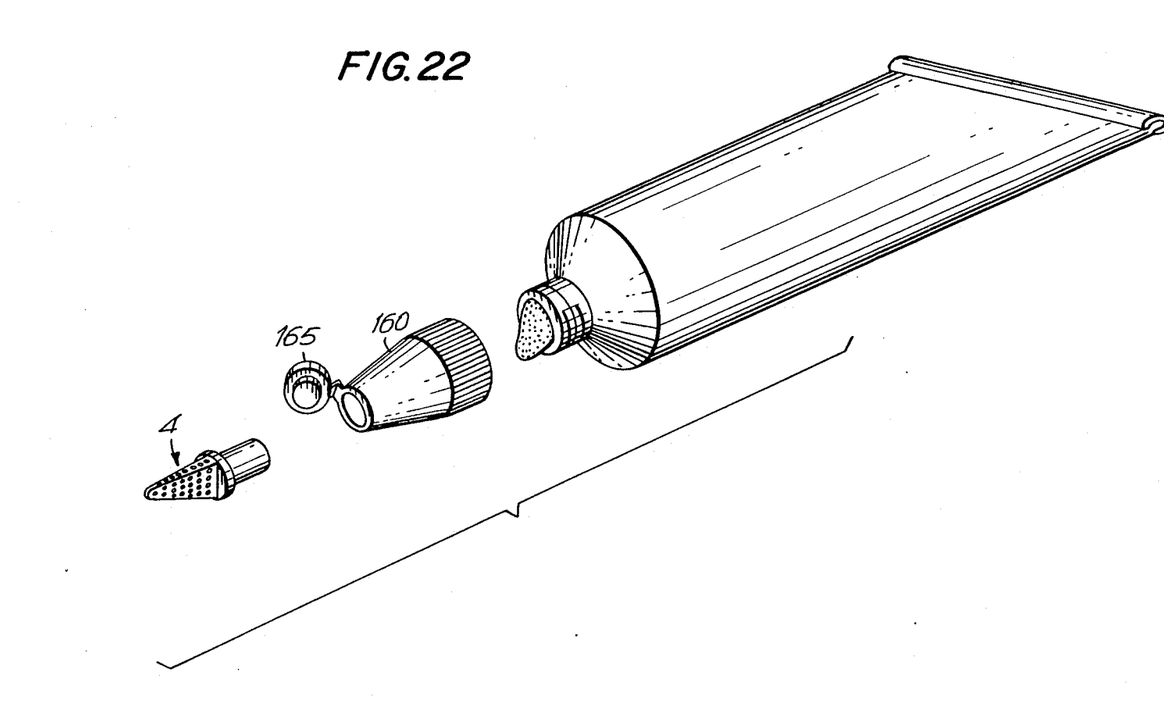
FIG. 22 is an exploded isometric view showing a further means for filling a dental tool with paste directly from a commercially available tube.
Figure 23:
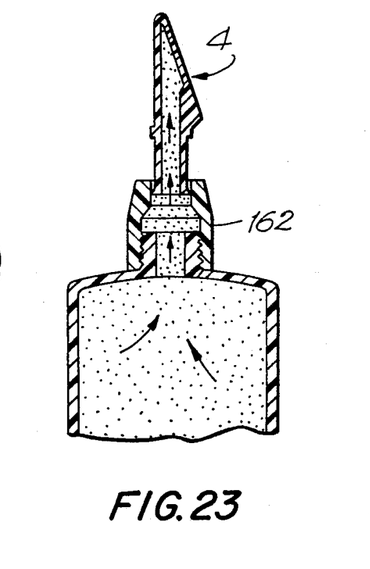
FIG. 23 is a cross-sectional view showing the filling means of FIG. 22 in place.
Figure 24:
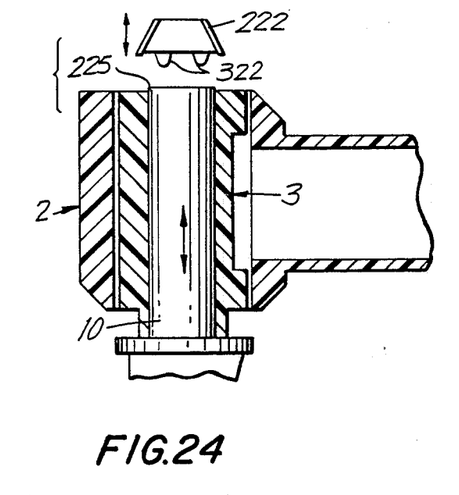
FIG. 24 is a side elevation view showing a manually pressed button cap.

FIGS. 21 through 23 depict alternative means for filling the dental tools with fluid material FIG. 21 shows a syringe-type device having an outlet stub of a diameter to fit tightly within the shank channel of a dental tool having a thin resilient membrane covering the grooves 12. When the syringe plunger 150 is depressed, paste within the syringe is pushed into an attached tool 4.

In FIGS. 22 and 23, a dispenser cap 160 is threadedly secured onto the external threaded opening stub 162 to a conventional toothpaste tube 164. The other end of the cap 160 has a plug opening which can receive the open end of a tool shank 10. The plug opening can be closed by a plug cap 165, hingedly secured to the dispenser cap 160.

The dental tool 4 after being filled with paste, can be pushed into and through the reciprocating sleeve 3 by squeezing the grooved shank 10 as shown in FIG. 15a, until the collar 11 protrudes beyond the distal end of the sleeve 3. The collar restrains the tool 4 from falling, or being pulled, out accidentally. The tapered spur 5 mates with the sleeve notch 6. The plunger 13 is lightly inserted into the shank channel 16 and the handpiece power is activated causing the tool 4 to reciprocate. Pressing downwardly against the outer cap surface 39 forces the plunger 13 into the shank channel 16, which causes the paste, or other fluid, to flow out through the perforations 18.

Figure 1:
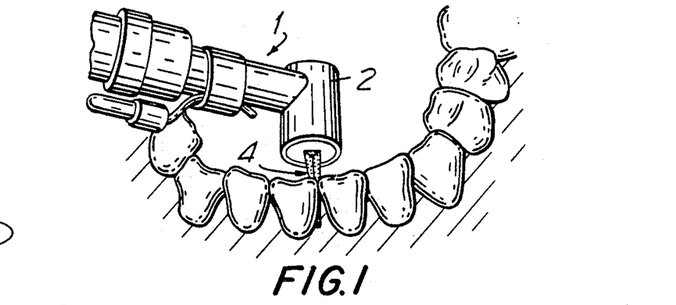
FIG. 1 is an isometric view of a reciprocating file tool combined with a reciprocating driver handpiece operating to clean the interdental spaces.

When the blade 4 is inserted into teeth interspaces, as shown in FIG. 1, the blade surfaces 27 will, e.g., polish the tooth surfaces. If the blade becomes lodged, and an excessive rotational moment is exerted, the spur 5 will flex and break away out of the notch 6, permitting rotation of the tool and preventing injury to the teeth. For this purpose, the spur should have a suitable flexural elastic modulus and thickness.

The tool 4 had been previously filled with a dosage of polishing paste, such as toothpaste, utilizing a tube cap dispenser, as shown in FIGS. 22 and 23.

The alternative embodiment of FIGS. 6 and 7 is prepared, filled with paste, and inserted into the handpiece in the same manner. If rotation restraint is desired, the sliding spring 22 is moved into engagement with the notched collar 23. If the dentist prefers a freely rotating tool, the spring can be left in the disengaged position, shown in FIG. 7, during use.

The limited rotation restraining means of the present invention can be used with tools fabricated from metal, and where there is no provision for dispensing of a fluid material.

Figures 10, 11:
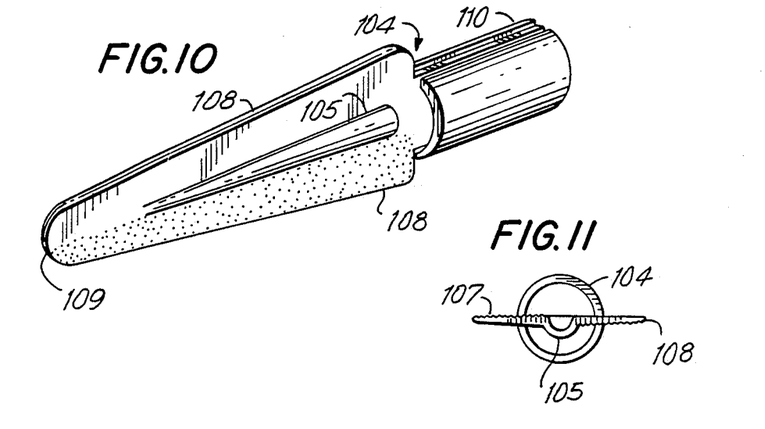
FIG. 10 is an isometric view of a dental tool fabricated of metal and having rotation-restraining means.
FIG. 11 is a bottom view of the tool of FIG. 10.
Figure 12:
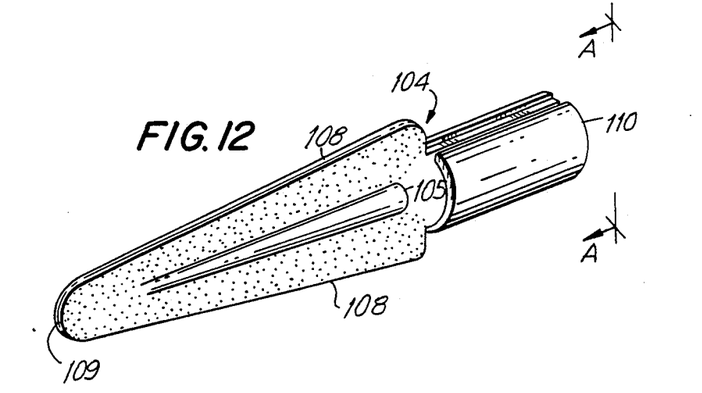
FIG. 12 is an isometric view of an alternative embodiment of a metal abrasive tool having twin file surfaces.

Referring to FIGS. 10 through 13, a file tool 104 is formed of stainless steel sheet material with a reinforcing groove 105, or corrugation, along the central axis of blade 106. The blade 106 is generally triangular in shape, tapering to a rounded apex 109 at its outer end. The blade also preferably is tapered towards its side edges 108. As shown in FIGS. 10 through 13, the major surfaces 107 of the blade can be coated with fine abrasive particles (such as diamond particles) on one complete side of the blade (FIG. 12) or on alternate surfaces (FIG. 10).

Figure 13:
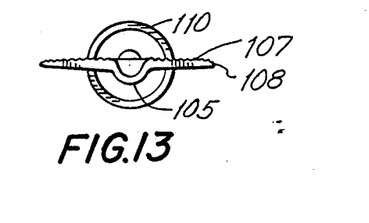
FIG. 13 is a bottom view of the tool of FIG. 12.
Figure 13A:
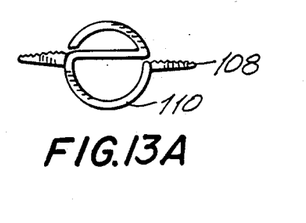
FIG. 13a is an end view taken along lines A—A of FIG. 12.

The shank 110 of this metal tool, can be shaped to provide a limited rotation restraint. As shown in FIG. 13a, the shank has an "S" configuration, being formed of an elastic spring metal, such as stainless steel.

Figure 17:
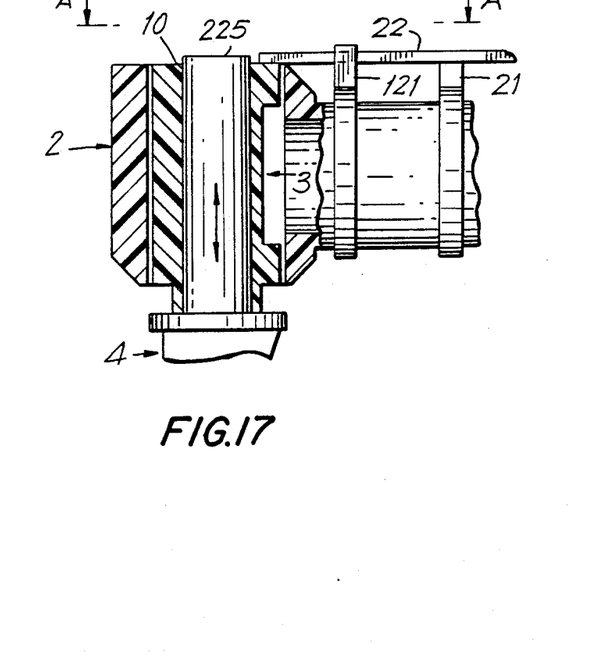
FIG. 17 is a cross-sectional view of the head of a dental handpiece showing a further embodiment of a rotation preventing device in accordance with the present invention.
Figure 18:
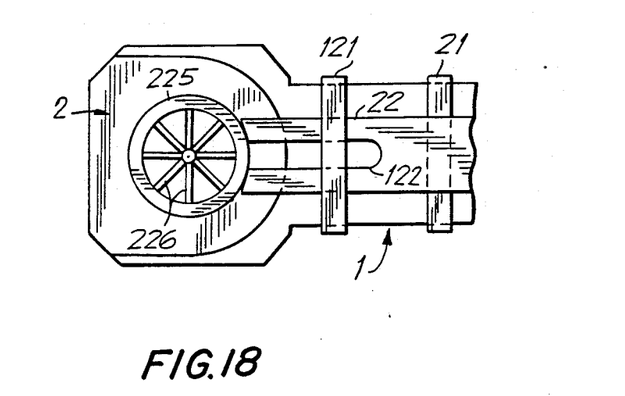
FIG. 18 is a view taken along lines A—A of FIG. 17

The metallic shank of the tool 104 is preferably sufficiently long so as to extend slightly beyond the distal end of the sleeve 3, such that the end of the shank 110 protrudes from the distal end of the sleeve 3 and a collar 111 is provided at the end of the shank 110 to prevent accidental removal. For this embodiment, the top of the shank can be provided on insert 225, inserted into the S-shaped shank 110, and including radiating bars 226, as is shown in FIGS. 17 and 18, or with a slot, facing upwardly. Rotation of this tool can be prevented by the spring leaf 22 (FIGS. 17 and 18), or by a manually pressed button cap 222, as shown on FIG. 25, (teeth or prongs 24, 322 project into the top opening of the shank 110. The end of the shank 110 can also be closed off and provided with slot or groove, opening outwardly towards the button cap 222 or spring leaf 22.

In yet another embodiment of this invention, the shank is preferably formed to have a normal diameter slightly larger than the internal diameter of the sleeve 103. When this S-shaped shank 110 is pressed into the sleeve 103, the lateral spring action of the shank preferably presses against the internal surface of the sleeve 3, preventing relative rotation between the sleeve 3 and the tool 104. The shank 110 extends to just below the end of the sleeve 103. Extending across, and connected to, the circumference of that distal end of the sleeve 3 is a series of radiating bars 130. The spaces between the bars 130 are sufficiently large to permit passage of the spring teeth 24, which prevent rotation of the sleeve 103, as explained above.

The effective flexibility of the spring leaf 22 can be varied manually by the provision of a second, and movable, set of holding arms 121, slidably secured to and on the outer surface of the spring leaf 22. By changing the linear location of the arms 121, i.e., along the major axial direction of the spring leaf 22, the length of the flexing leaf 22 is varied.

The force required to flex the leaf 22 is inversely proportional to its length, i.e., the distance from the apex of the cleft 122, or of the teeth 24, to the retention arms 21, 121. In this embodiment, the second set of holding arms 121 acts as a movable fulcrum for the flexible spring leaf 22, such that when the arms 121 are holding the leaf 22, adjacent the teeth 24, the effective flexibility of the spring leaf is at its minimum, but when the holding arms 121 are adjacent the stationary holding arms 21, or removed completely, the flexibility of the spring leaf is at its maximum.

The patentable embodiments which are claimed are as follows:

1. In a dental device comprising reciprocating drive means, a sleeve member operatively connected to the drive means for reciprocating motion, and designed to retain a dental tool, and a dental tool having a shank and a blade portion and being retained ins aid sleeve by said shank, the improvement comprising an internal channel extending axially along a central portion of the shank, and a plenum chamber within the blade portion in fluid flow connection with the shank channel, outlet openings through the blade surface, and pressure means and closure means for the shank channel, operable to force any fluid material within the channel and plenum out through the outlet openings.

2. In the dental tool having a shank and a relatively thin flat blade portion, a spine extending along the blade from the shank, the spine having a greater thickness than the blade portion, the shank being designed to be retained by a sleeve in a reciprocating dental tool drive means, the improvement comprising an internal channel extending axially along a central portion of the shank, and a plenum chamber within the blade portion in fluid flow connection with the shank channel, outlet openings through the blade surface, and pressure means and closure means for the shank channel, operable to force any fluid material within the channel and plenum out through the outlet openings.

3. The dental tool of claim 2, wherein the spine is colinear with the shank, and extends along not more than 75% of the full length of the blade portion.

4. The dental tool of claim 2, wherein the pressure means comprises a plunger cap comprising a piston portion slidably and removably secured within the shank channel and a cap having a diameter greater than that of the piston portion and extending beyond the shank, the cap being designed to be manually depressed.

5. The dental tool of claim 4, comprising an elongated strap means secured at one end to the cap and at the other end to the shank, whereby the plunger cap is permanently secured to the shank and blade portions of the dental tool.

6. The dental tool of claim 2, wherein the pressure means comprises a reservoir member secured to the end of the shank and designed to extend outside of the shank in a direction away from the blade portion, the reservoir member comprises a chamber defined by at least one wall proximal to the shank and which is flexibly corrugated to permit reciprocating movement of the dental tool without corresponding translational movement of the entire reservoir member within the expected range of reciprocating stroke amplitude.

7. The dental tool of claim 2, wherein the blade portion comprises a pair of flexible walls extending from the spine laterally to a common edge.

8. The dental tool of claim 7, wherein the common edge has a thickness of not greater than about 0.01 in.

9. The dental tool of claim 7, wherein the flexible walls each have a thickness of at least about 0.005 in.

10. In a dental device comprising reciprocating drive means, a sleeve member operatively connected to the drive means for reciprocating motion, and designed to retain a dental tool, and a dental tool having a shank and a blade portion and being retained in said sleeve by said shank, the improvement comprising a flexible projection extending outwardly from the dental tool shank, adjacent the blade portion, the projection extending longitudinally along the shank and radially outwardly from the shank and a concave surface formed on the proximal edge of the sleeve, the projection and concave surface being in mating juxtaposition during operation of the dental device to provide limited restraint against rotation of the dental tool relative to the drive means.

11. The dental device of claim 10 wherein the flexible projection is tapered in the direction of the apex of the concave surface and the concave surface has a matching taper.

12. The dental device of claim 10, comprising a slide member secured to the drive means, a spring finger secured to the slide means and extending towards the sleeve, and a collar surrounding the outer edge of the shank and extending beyond the end of the sleeve distal the blade portion, wherein the flexible projection is formed adjacent the end of the spring finger and the concave surface is formed on the circumference of the collar, the spring finger being slidably movable into and out of engagement with the collar.

13. The dental device of claim 12, wherein the spring finger is formed of a metal, and the collar is formed of a material selected from the group consisting of elastomers and polymers.

14. The dental device of claim 10, wherein the dental tool is integrally formed of a material selected from the group consisting of elastomers and polymers.

15. The dental device of claim 10, wherein the dental tool is integrally formed of a metal.

16. A method for cleaning and polishing teeth, comprising filling with a cleansing fluid the interior plenum chamber of a hollow dental tool, the dental tool comprising a shank and a blade member and outlet perforations for the plenum chamber extending through the operating edge of the blade portion, securing the dental tool to a reciprocating drive means and reciprocatingly driving the tools along the surfaces of a patient's teeth while dispensing the cleansing fluid under pressure out through the outlet perforations by manually exerting pressure in the plenum chamber.

17. In a dental device comprising reciprocating drive means, a sleeve member operatively connected to the drive means for reciprocating motion, and designed to retain a dental tool, and a dental tool having a shank and a blade portion and being retained in said sleeve by shank, a slide member slidably secured to the drive means, the improvement comprising a spring finger secured to the slide means and extending towards the sleeve, and a collar surrounding the outer edge of the shank and extending beyond the end of the sleeve distal the blade portion, a flexible projection extending from adjacent the end of the spring finger proximal the sleeve, and a concave surface formed on the circumference of the collar, the spring finger being slidably movable into and out of engagement with the collar, the projection and concave surface being in mating juxtaposition during operation of the dental device to provide limited restraint against rotation of the dental tool relative to the drive means.

* * * * *